Figure 1:
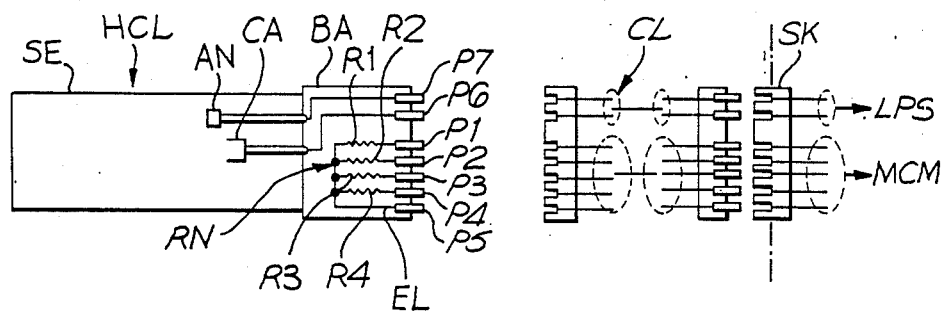

United States Patent [19]

Stockdale et al.

[11] Patent Number: 4,669,879
[45] Date of Patent: Jun. 2, 1987

[54] ATOMIC RESONANCE LINE SOURCE LAMPS AND SPECTROPHOTOMETERS FOR USE WITH SUCH LAMPS

[75] Inventors: Trevor J. Stockdale, Over; Peter Morley, Newmarket, both of England

[73] Assignee: U.S. Philips Corporation, New York, N.Y.

[21] Appl. No.: 894,451

[22] Filed: Aug. 4, 1986

Related U.S. Application Data

[63] Continuation of Ser. No. 744,648, Jun. 13, 1985, abandoned, which is a continuation of Ser. No. 436,205, Oct. 25, 1982, abandoned.

[30] Foreign Application Priority Data

Nov. 11, 1981 [GB] United Kingdom ............... 8133968

[51] Int. Cl.[4] ............................ G01J 3/10; G01J 3/42
[52] U.S. Cl. ..................................... 356/326; 315/71; 356/312; 356/315; 364/498
[58] Field of Search ............... 356/312, 314, 315, 319, 356/323–326, 328; 315/52, 58, 71, 129; 354/275; 364/498, 526

[56] References Cited

U.S. PATENT DOCUMENTS

| | | | |
|---|---|---|---|
| 3,670,638 | 6/1972 | Lindsay | 354/275 |
| 3,810,200 | 5/1974 | Sakaguchi et al. | 354/275 X |
| 3,898,501 | 8/1975 | Hosoya et al. | 356/314 X |
| 4,024,557 | 5/1977 | Aoyama et al. | 354/275 |
| 4,300,834 | 11/1981 | Demers et al. | 356/316 |

FOREIGN PATENT DOCUMENTS

| | | | |
|---|---|---|---|
| 2852949 | 6/1980 | Fed. Rep. of Germany | 354/275 |
| 52-55686 | 5/1977 | Japan | 356/319 |
| 2031171 | 4/1980 | United Kingdom | 354/275 |

OTHER PUBLICATIONS

Baird brochure, *Plasma/AFS Atomic Fluorescence Spectrometer*, 1981.

Primary Examiner—F. L. Evans
Attorney, Agent, or Firm—Paul R. Miller

[57] ABSTRACT

The present invention is directed to a lamp assembly for use in atomic absorption spectrometers in which an atomic element hollow cathode lamp assembly has a lamp formed by a hollow cathode electrode and an anode electrode within a sealed envelope. A base structure is attached to the envelope, and located within the base structure is a resistor network consisting of four resistors connected to a common lead and having four plug terminals protruding from the base structure. Two further plug terminals also protruding from the base structure are connected respectively to the cathode and anode electrodes to provide a connecting structure for connecting these electrodes to a lamp power supply. The five plug terminals protruding from the base structure and connected respectively to the resistors and the common lead provide a further connecting structure of the resistor network to a measurement circuit in an atomic absorption spectrophotometer. The resistor network represents the atomic element of the lamp by virtue of two of the resistors, and further, represents a lamp operating current by virtue of the other two resistors. All of the plug terminals are arranged in a conventional octal plug configuration with a boss on the base structure for insuring correct electrical connection.

34 Claims, 5 Drawing Figures

ATOMIC RESONANCE LINE SOURCE LAMPS AND SPECTROPHOTOMETERS FOR USE WITH SUCH LAMPS

This is a continuation of application Ser. No. 744,648, filed June 13, 1982, now abandoned, which is a continuation of previous U.S. application Ser. No. 436,205, filed Oct. 25, 1982, now abandoned, and all benefits are hereby claimed for this application.

This invention relates to atomic resonance line source lamps and spectrophotometers using such lamps.

Atomic absorption spectrophotometer source lamp assemblies are known having a lamp for producing resonance line radiation characteristic of one or more atomic elements when operated by lamp power supply means. Atomic absorption spectrophotometers are also known including a monochromator for passing radiation of a selected wavelength characteristic of an atomic element when that radiation is emitted by a source lamp for producing resonance line radiation, and wavelength control means responsive to wavelength information applied thereto for setting the monochromator to the selected wavelength.

Such known lamp assemblies are labelled to identify the one or more atomic elements to the person using the spectrophotometer who then has the task of entering into such known spectrophotometers the wavelength information for setting the monochromator. Disadvantages of this task are that it involves the possibility of error on the part of the user and also limits the extent of possible automatic operation of the spectrophotometer.

An object of the invention is to overcome these disadvantages.

According to the invention there is provided a source lamp assembly as described in the second paragraph of this specification, characterised in that the lamp assembly includes an electrical network representative of said one or more atomic elements and connecting means for connecting the network to measurement circuit means in an atomic absorption spectrophotometer enable identification of the one or more atomic elements in the spectrophotometer.

Also according to the invention there is provided an atomic absorption spectrophotometer as described in the second paragraph of this specification, characterised in that the spectrophotometer is adapted for use with a source lamp assembly as described in the previous paragraph with the spectrophotometer including the measurement circuit means, a microprocessor and a read-only memory holding wavelength information at a location therein associated with each of the respective one or more atomic elements of a plurality of the lamp with the microprocessor being conditioned to identify the one or more atomic elements of the lamp assembly whose network is connected to the measurement circuit means responsive to measurement of the respective network by the measurement circuit means, and the microprocessor being conditioned to apply to the wavelength control means wavelength information derived from the read-only memory for an atomic element which is so identified.

Known lamp assemblies as described in the second paragraph of this specification and in which the lamps are single atomic element or multiple atomic element hollow cathode lamps are labelled to identify a maximum lamp operating current to the person using the spectrophotometer who then has the task of choosing and putting into effect a suitable lamp operating current. This again involves the possibility of error and limits the extent of possible automatic operation.

In a lamp assembly which is according to the invention and furthermore in which the lamp is a single atomic element or multiple atomic element hollow cathode lamp. the network may be further representative of a lamp operating current. An advantage here is that during the useful lifetime of a spectrophotometer the characteristics of a hollow cathode lamp for a particular atomic element or combination of atomic elements, in particular the maximum lamp operating current, may change. A spectrophotometer according to the invention may be adapted for use with such a source assembly with the spectrophotometer including the lamp power supply means and the read only memory holding lamp current information, the microprocessor being conditioned to control the lamp power supply means using, together with the lamp current information from the read-only memory, further lamp current information derived by the measurement circuit means from the lamp assembly network connected thereto.

In a spectrophotometer according to the invention, an analysis consisting of the operation of the spectrophotometer to analyse one or more samples in respect of an atomic element of a lamp assembly may be controlled by the microprocessor being conditioned to use an information set continuously stored in a read-write memory for at least the duration of that analysis, in which case the information set has atomic element related information, including wavelength information, derivable from the read-only memory for that atomic element, together with sample related information derivable from elsewhere for the one or more samples. Both atomic element related information and sample related information are needed for an analysis, and bringing them both into such an information set in the manner described for use by the microprocessor has the advantage of further facilitating automatic operation of the spectrophotometer in an analysis using a lamp assembly according to the invention.

A spectrophotometer as described in the previous paragraph may have holding and positioning means for holding more than one lamp assembly at a time with the networks of all the lamp assemblies so held being connected to the measurement circuit means and for positioning one lamp at a time of the lamp assemblies so held in the optical path of the monochromator, in which case an analysis sequence consisting of the operation of the spectrophotometer to analyse one or more samples in respect of each of a set of atomic elements in turn, wherein the source lamp for each atomic element of the set is part of the lamp assembly, is controlled by the microprocessor being conditioned to control the holding and positioning means to position a lamp emitting radiation characteristic of each atomic element of the set of elements in turn in the optical path of the monochromator and by the microprocessor being conditioned two use each of a plurality of information sets in turn, one information set for each atomic element of the set of elements with, the plurality of information sets being continuously stored in the read-write memory for at least the duration of the analysis sequence. This arrangement has the advantage of facilitating automatic operation of the spactrophotometer in such an analysis sequence in respect to a set of atomic elements.

Figure 2:
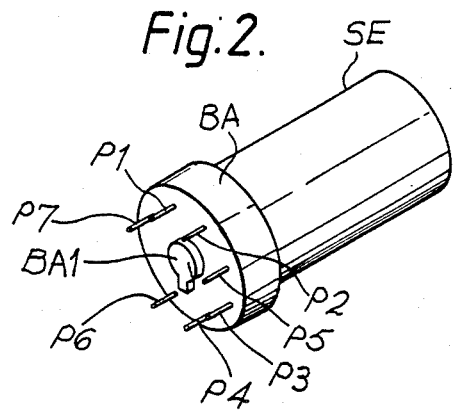
Figure 3:
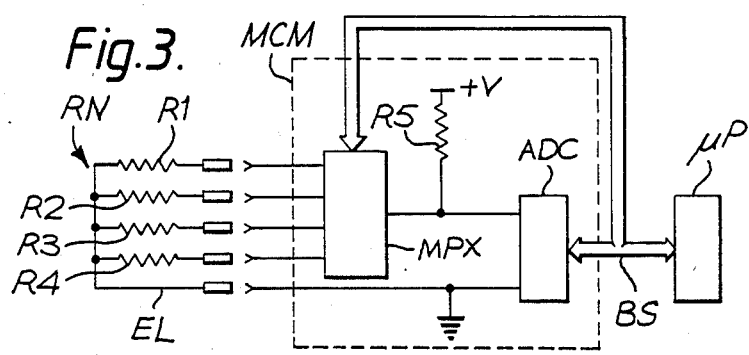
Figure 4:
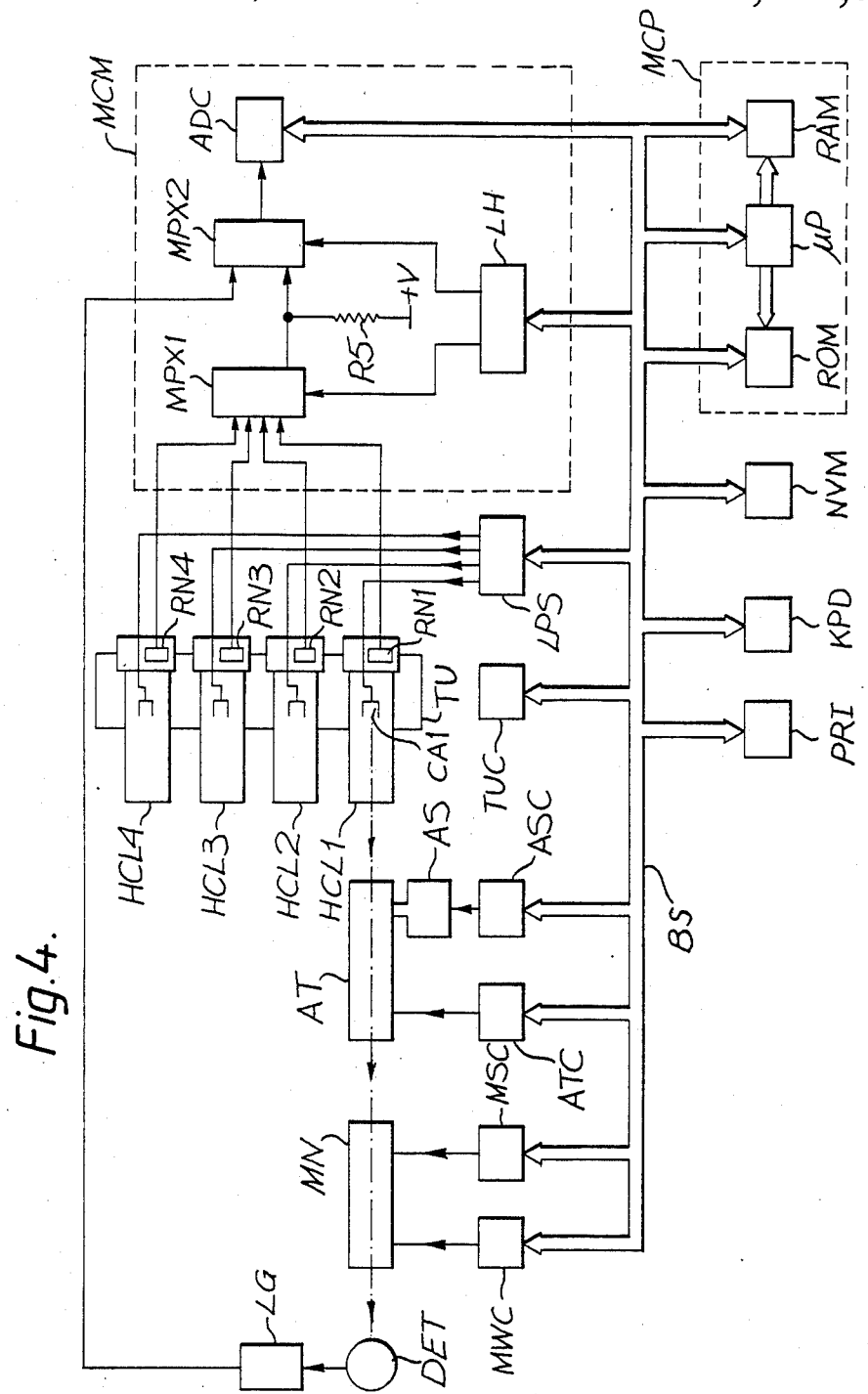
Figure 5:
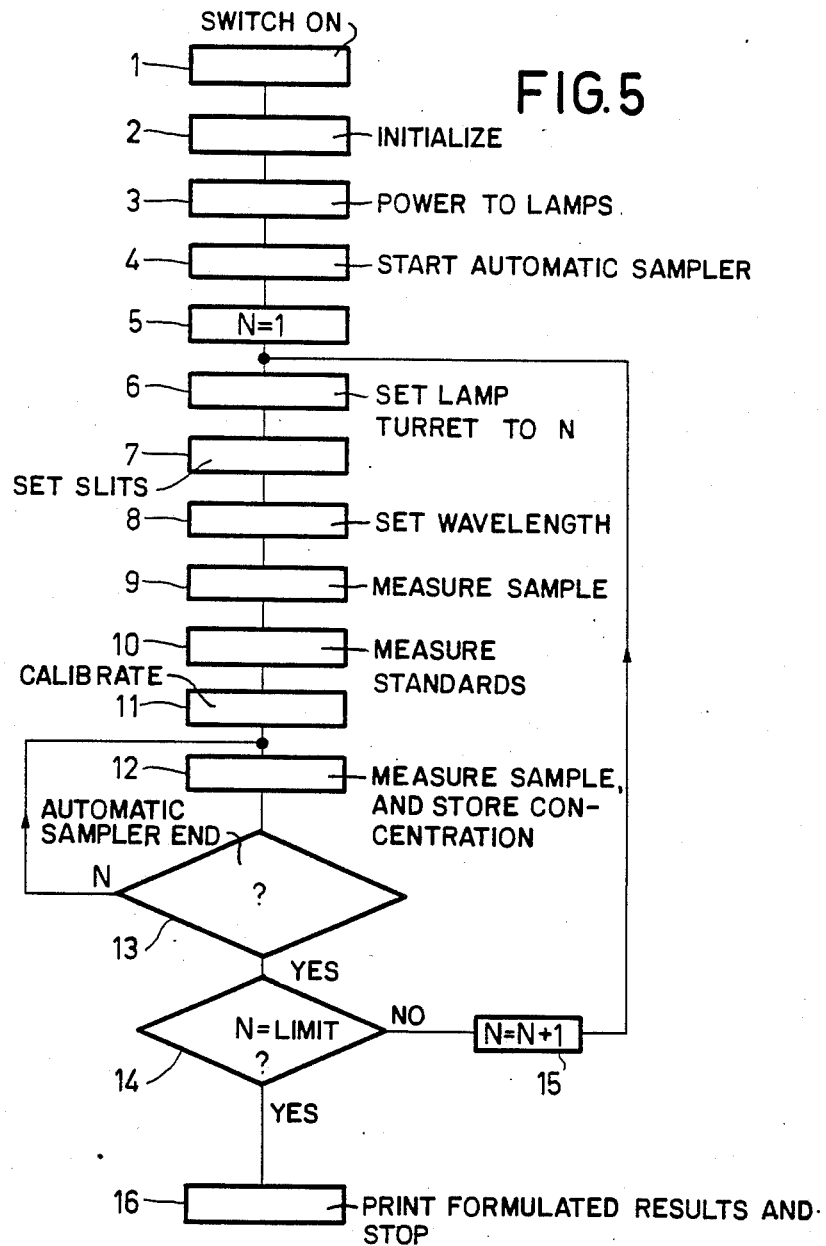

The invention will now be described in more detail with reference to the accompanying drawings in which:

FIG. 1 shows a schematic section view of a single atomic element hollow cathode lamp assembly according to the invention and electrical connectors directly associated therewith, FIG. 2 shows a perspective view of the lamp assembly of FIG. 1, FIG. 3 shows the resistor network of the lamp assembly of FIG. 1 and measurement circuit means of a spectrophotometer using that lamp, FIG. 4 shows an atomic absorption spectrophotometer according to the invention using four lamp assemblies as in FIG. 1, and FIG. 5 is a flow chart of an operation of the spectrophotometer shown in FIG. 4.

Referring now to FIGS. 1 and 2, a single atomic element hollow cathode lamp assembly HCL has a lamp formed by a hollow cathode electrode CA and an anode electrode AN within a sealed envelope SE. A base BA is attached to the envelope SE, and located within the base BA is a resistor network RN consisting of four resistors R1, R2, R3 and R4 connected to a common lead EL. Two plug terminals p6 and p7 protruding from the base BA and connected respectively to the electrodes CA and AN provide connecting means for connecting these electrodes to lamp power supply means LPS (see FIG. 4). Five plug terminals P1 to P5 protruding from the base BA and connected respectively to the resistors R1 to R4 and the lead EL provide further connecting means for including the resistor network in measurement circuit means MCM (see FIGS. 3 and 4) in an atomic absorption spectrophotometer. The resistor network is representative of the atomic element of the lamp by virtue of the resistors R1 and R2 and is furthermore representative of a lamp operating current by virtue of the resistors R3 and R4. As shown in FIG. 2, the terminals P1 to P7 are arranged in a conventional octal plug configuration with a boss BA1 on the base BA for ensuring correct electrical connection.

When in the operative position in a spectrophotometer, the lamp assemblY HCL will be located in the optical path thereof and electrical connection from the terminals P1 to P7 to a fixed socket SK in the spectrophotometer will be made via a connecting lead CL with socket and plug connectors. Instead of being located within the base BA the resistor network RN could possibly be located within the connecting lead CL, and in this case the lead CL can be cx;nsidered as forming part of the lamp assembly with appropriate parts of the lead CL providing part of the connecting means for the electrodes and providing the whole of the further connecting means for the network. Another possibility would be to locate the network RN inside the sealed envelope SE. Both these possible variations from the arrangement shown in FIGS. 1 and 2 indicate that it is not necessary for the lamp to be provided with a separately identifiable base.

Referring now to FIG. 3, the resistor network RN is shown together with measurement circuit means MCM and a microprocessor μP in a spectrophotometer. The measurement circuit means MCM includes a multiplexer MPX and an analogue-to-digital converter ADC respectively controlled by and connected to the microprocessor μP via a bus BS, and a resistor R5 connected to a voltaqe source +V. By means of the multiplexer MPX the resistors R1 to R4 are connected in turn in series with the resistor R5 and the common lead EL and hence the voltage across each of the resistors R1 to R4 in turn is applied to the analoque-to-diqital converter ADC. The ohmic values of the two resistors R1 and R2 together represent the atomic element of the single atomic element hollow cathode lamp assembly incorporating the network; conveniently one of these two resistors represents the tens value and the other resistor represents the units value of the atomic number of the atomic element. The ohmic values of the two resistors R3 and R4 together represent a lamp operating current; conveniently the maximum operating current for the electrodes of the lamp assembly incorporating the network. The microprocessor μP is conditioned to identify the atomic element responsive to measurement of the resistor network by the measurement circuit means MCM, that is to say the two successive digital outputs of the converter ADC responsive to the resistors R1 and R2. The lamp current information derived by the measurement circuit means MCM from the resistor network, that is to say the two successive digital outputs of the converter ADC responsive to the resistors R3 and R4, is used by the microprocessor μP together with other lamp current information, as will be described in detail with reference to FIGS. 4 and 5, to control the lamp power supply means LPS connected to the electrodes of the respective hollow cathode lamp.

It will be appreciated that although the resistive network as described is inexpensive and convenient the electrical network incorporated in the hollow cathode lamp assembly as described above to represent the atomic element and the maximum lamp operating current could be other than resistive. With suitably adapted measurement circuit means, the network could for example be capacitive or it could provide a binary representation by using connections which are open or short circuit or by using diodes.

The single atomic element hollow cathode lamp provided with an electrical network as described above with reference to FIGS. 1 and 2 is one example of a lamp assembly according to the invention. Other lamps for producing resonance line radiation characteristic of one or more atomic elements when operated by lamp power supply means may he provided with similar networks to form atomic absorption spectrophotometer source lamp assemblies according to the invention. One such other lamp is an electrodeless discharge lamp. In this case an electrical network may be similarly provided in an assembly with the lamp to enable the single atomic element for which the lamp emits resonance line radiation to be identified in the spectrophotometer. Electrodeless discharge lamps are usually provided with an auxiliary power supply external to the spectrophotometer. The network in the lamp assembly in this case could also represent a particular value of electrical power which is identified in the spectrophotometer and used to control the auxiliary power supply. Another such lamp is a multiple atomic element hollow cathode lamp. In this case also an electrical network may be provided in an assembly with the lamp to enable all the atomic elements for which the lamp emits resonance line radiation to be identified in the spectrophotometer. Multiple atomic element hollow cathode lamps conventionally emit resonance line radiation for particular combination of two, three or four atomic elements, and the network could represent these atomic elements individually or it could represent the particular combination. The network could also represent a maximum lamp current in a manner similar to that described above for a single atomic element hollow cathode lamp.

Referring now to FIG. 4, there is shown an atomic absorption spectrophotometer holding four single atomic element hollow cathode lamp assemblies HCL1 to HCL4 each in accordance with the lamp assembly HCL described above with reference to FIGS. 1 and 2 and each connected to measurement circuit means MCM and a microprocessor μP essentially as described above with reference to FIG. 3. The four lamp assemblies HCL1 to HCL4 are held in a turret TU operated by turret control means TUC to position a selected one of the four lamp assemblies HCL1 to HCL4 at a time in the optical path of the spectrotometer. FIG. 4 shows the lamp assembly HCL1 in the optical path. Radiation emitted by the lamp assembly HCL1 passes from the respective cathode CA1 through an atomiser AT which may be of the conventional flame type or electrothermal furnace type. Samples to be analysed by the spectrophotometer are fed into the atomiser AT from an automatic sampler AS operated by automatic sampler control means ASC and the atomiser is operated by atomiser control means ATC. Having passed through the atomiser AT, the radiation passes through a monochromator MN. The wavelength of the radiation passed by the monochromator MN is selected by wavelength control means MWC and the bandpass, that is to say the slit width, of the monochromator MN is selected by slit control means MSC. A photomultiplier tube detector DET provides an electrical voltage signal whose amplitude is proportional to the intensity of radiation emerging from the monochromator MN, and a logarithmic converter LG provides an amplified voltage signal proportional to the logarithm of the output of the detector DET. The concentration of the atomic element in respect of which the samples presented to the atomiser AT are analysed is essentially proportional to the output signal of the logarithmic converter LG.

The two electrodes of each of the lamp assemblies HCL1 to HCL4 are connected to the lamp power supply means LPS with only the hollow cathode electrodes CA1 etc being schematically shown in the Figure with a single connection in each case. The resistor networks RN1 to RN4 of the respective lamp assemblies HCL1 to HCL4 with each network having four respective resistors R1 to R4 as shown in FIGS. 1 and 3, are connected to a multiplexer MPX1. For simplicity of illustration onlY one connection is shown from each of the networks RN1 to RN4 to the multiplexer MPX1 although there is an individual connection from each of the sixteen resistors therein to the multiplexer MPX1. Each of these sixteen network resistors is connected in turn in series with the resistor R5 to the voltage source +V via the multiplexer MPX1 controlled by latch circuit means LH. The voltage across each of the sixteen network resistors is connected in turn to the analogue-to-digital converter ADC via a further multiplexer MPX2 which is also controlled by the latch circuit means LH. The multiplexers MPX1 and MPX2, the resistor R5, the voltage source +V, the latch circuit means LH and the analogue-to-digital converter ADC form the measurement circuit means MCM to which the networks RN1 and RN4 are connected. The output signal of the logarithmic converter LG is also connected to the analogue-to-digital converter ADC via the multiplexer MPX2. In operation of the spectrophotometer the networks RN1 to RN4 are measured by the measurement circuit means MCM as soon as the lamp assemblies HCL1 to HCL4 are connected thereto. Thereafter this measurement is repeated as a background check routine which is interrupted when it is necessary for another analogue signal produced by the spectrophotometer, for example the output of the logarithmic converter LG, to be applied to the analogue-to-digital converter ADC via the multiplexer MPX2. The background check routine can be used, for example, to provide an error signal if a lamp is not present in a required position.

A microcomputer MCP includes the microprocessor μP, a volatile read-write memory RAM for temporarily holding data for processing by the microprocessor μP, and a read-only memory ROM holding program information for conditioning the operation of the microprocessor μP. The bus BS connects the microprocessor μP to the read-write memory RAM, to the read-only memory ROM, to the analogue-to-digital converter ADC, to the latch circuit means LH, to the lamp power supply LPS, to the turret control means TUC, to the automatic sampler control means ASC, to the atomiser control means ATC, to the slit control means MSC and to the wavelength control means MWC.

In addition to holding program information the read-only memory ROM also holds atomic element related information, including in particular wavelength information, at a location therein associated with the respective atomic element of each of a plurality of single atomic element hollow cathode lamp assemblies with which the spectrophotometer may be used. There may be in excess of sixty such single atomic element hollow cathode lamp assemblies but at any one time only one or some of these lamp assemblies, for example the four lamp assemblies HCL1 to HCL4, will be located in the spectrophotometer with their networks connected to the measurement circuit means MCM. The microprocessor μP is conditioned to identify the atomic element of the one or more lamp assemblies whose networks are connected to the measurement circuit means MCM responsive to measurement of the respective network thereby. In the case of the four lamp assemblies HCL1 to HCL4 shown in FIG. 4 this identification is responsive to the output of the analogue-to-digital converter ADC in respect of the voltages measured successively across the resistors R1 and R2 of the respective networks RN1 to RN4 of the lamp assemblies. The microprocessor μP is further conditioned to apply to the wavelength control means MWC wavelength information derived from the read-only memory ROM for that one of the one or more lamp assemblies whose atomic elements are identified and the lamp of which furthermore is present in the optical path of the monochromator. The turret TU and turret control means TUC include means which enable the microprocessor μP to identify the lamp present in the optical path of the monochromator.

The read-only memory ROM also holds lamp current information. The microprocessor μP is conditioned to control the lamp power supply means LPS using this lamp current information for the one or more lamp assemblies whose atomic elements are identified via the measurement circuit means MCM. It is advantageous for the microprocessor μP to use the maximum lamp current information derived from the networks RN1 to RN4 via the measurement circuit means MCM together with the lamp current information derived from the read-only memory ROM to control the lamp power supply means LPS. If the networks RN1 to RN4 did not contain the resistors R3 and R4 representative of the maximum lamp operating current of the respective lamp assemblies, then the lamp current information in the read-only memory ROM could be held at locations therein associated with the respective atomic element of each of the plurality of hollow cathode lamp assemblies with which the spectrophotometer may be used and could entirely define the operating current for the respective lamps.

For an analysis consisting of the operation of the spectrophotometer to analyse one or more samples in respect of the single atomic element of one of the plurality of hollow cathode lamp assemblies for which information is stored in the read only memory ROM, both atomic element related information and sample related information are needed. Automatic operation of the spectrophotometer is facilated by both types of information being brought together to form an information set which is continuously stored for at least the duration of that analysis in a non volatile read-write memory NVM. The microprocessor μP is connected by the bus BS to the memory NVM and is conditioned to use that information set to control that analysis The atomic element related information for each information set in the memory NVM is derivable from the read-only memory ROM and transferred thereto by the microprocessor μP upon identification of the atomic element of the respective lamp assembly. This atomic element related information will include the wavelength information already mentioned together with slit width information for application to the slit control means MSC. In the case where the atomiser AT is of the flame type, the atomic element related information derivable from the read-only memory ROM will include information identifying fuel type and fuel rate for application to the atomiser control means ATC and may also include measurement time information. The time for which the output signal of the detector DET, received via the logarithmic converter LG, multiplexer MPX2 and analogue-to-digital converter ADC, is averaged by the microprocessor μP for noise reduction of that signal is determined by the measurement time. In the case where the atomiser AT is of the electrothermal furnace type, the atomic element related information will again include wavelength information and slit width information, it will furthermore include furnace heating cycle information for application to the atomiser control means ATC, and it may include measurement time information relevant to determining peak height and peak area results from the output signal of the detector DET.

The sample related information for each information set in the memory NVM may be entered into an appropriate location therein by the user of the spectrophotometer via a keypad KPD connected by the bus BS to the microprocessor μP. This sample related information will include the number of standard concentration samples to be held in the automatic sampler AS and information identifying the concentration of those standard samples. The feature of background correction, which is well known and therefore not otherwise mentioned in this specification, will normally be provided for use in the spectrophotometer and the sample related information will in this case also indicate whether or not background correction is to be used in a particular analysis. The atomic element related information may also include an overriding instruction to switch off background correction for atomic elements for which the wavelength of radiation to be passed by the monochromator is above a certain value.

The results of an analysis of one or more samples in respect of a single atomic element are temporarily stored in the volatile read-write memory RAM of the microcomputer MCP and eventually outputted to a suitable recorder, for example a printer PRI shown connected by the bus BS to the microprocessor μP, and possibly also to a display (not shown).

It is convenient to mention here that the automatic sampler AS will be of a type specifically appropriate for use either with a flame type atomiser AT or an electrothermal furnace type atomiser AT as the case may be. Furthermore the automatic sampler control means ASC will normally partly be specific to and located in the particular automatic sampler AS and partly be permanently associated with the microprocessor μP and located in the main body of the spectrophotometer. It is well known for atomic absorption spectrophotometers to be primarily provided with one type of atomiser and to be adaptable for use with the other type of atomiser as an accessory. For example it is known to have an atomic absorption spectrophotometer which is primarily for use in the flame mode but adaptable for use in the electrothermal mode; and in this case the atomiser control means ATC for the electrothermal furnace will normally be provided as an accessory with that furnace rather than being located in the main body of the instrument and permanently associated with the microprocessor μP. Appropriate sensors (not shown) will be provided so that the type of atomiser AT and automatic sampler AS are identified to the microprocessor μP for appropriate operation. In the case mentioned where the atomiser control means ATC is provided as an accessory part of the spectrophotometer it can have its own non-volatile read-write memory to hold a plurality of sets of furnace heat cycle information, and this information which has been mentioned above as being derivable from the read-only memory ROM may instead remain in the non-volatile read-write memory of the electrothermal furnace atomiser control means ATC which may then be considered as part of the non-volatile read-write memory NVM holding the total information set for an analysis.

The non-volatile read-write memory NVM has the capacity to store a plurality of information sets as described above. Thus an analysis sequence consisting of the operation of the spectrophotometer to analyse one or more samples held in the automatic sampler AS in respect to each of a set of atomic elements in turn is controlled by the microprocessor μP being conditioned to use each of the plurality of information sets in turn, one information set for each atomic element of the set of elements. The plurality of information sets will be continously stored in the read-write memory NVM for at least the duration of the analysis sequence. For example, the memory NVM will have the capacity to store at least four information sets, one for each of the four single atomic element hollow cathode lamp assemblies HCL1 to HCL4 shown in FIG. 4. With the use of four such lamp assemblies, the atomic element related information in each information set is derivable from the read-only memory ROM. The spectrophotometer may additionally be able to use lamps other than the lamp assemblies according to the invention which have networks identifying the respective atomic element. For example in each of the four turret lamp locations there may be accommodated a conventional single atomic element hollow cathode lamp. In this case the user of the spectrophotometer may simply provide, via the keypad KPD, information to the microprocessor μP identifying the atomic element of each lamp and in response thereto the microprocessor μP can derive all the necessary atomic element related information from the read-only memory ROM and transfer it for use into the non-volatile memory NVM. In a more precise reproduction of the function of any one of the resistor networks RN1 to RN4, the user could also provide information via the key pad KPD corresponding to the lamp current information of those networks. As another example, conventional electrodeless discharge lamps may beaccommodated in each of the four turret lamp locations. In this case again the user will provide via the key pad KPD information identifyinq the respective atomic element of the lamp, and additionally the user will have to provide information for an auxiliary power supply for operating electrodeless discharge lamps. As another example, multiple atomic element hollow cathode lamps may be used. These lamps may be conventional, in which case the user will provide via the keypad KPD information identifying the lamp as a multiple element lamp, information identifying the atomic elements of the lamp and lamp current information. A possible modification is that the multiple atomic element hollow cathode lamp may be provided with a resistor network, to be measured by the measurement circuit means MCM, by which it will provide lamp current information and information identifying it as a multielement lamp. The user will then provide information via the keypad KPD identifying the atomic elements of the lamp and the microprocessor μP will be conditioned to derive atomic element related information from the read only memory ROM and transfer it to a separate information set in the non-volatile read-write memory NVM for each of those atomic elements.

In addition to the ability to use lamps other than the lamp assemblies according to the invention, the spectrophotometer may be provided with a manual override facility such that even when a lamp assembly having a network according to the invention is present the user will be able to enter, via the keypad KPD, atomic element related information into an information set in the non-volatile read-write memory NVM which is different to the information which would otherwise be derived from the read-only mesory ROM.

An external computer (not shown) may be connected via a suitable interface circuit to the bus BS. One use of an external computer can be to further facilitate automatic operation of the spectrophotometer by augmenting the function of the non-volatile read-write memory NVM. For example once an information set consisting of atomic element related information and sample related information as described above has been entered into the non-volatile memory NVM for a particular analysis, that information set may be transferred to the external computer for recall at any later date for use in repetition of the same analysis even though the capacity of the non-volatile memory NVM may have been fully used for different analyses in the meantime.

It will be appreciated that in the above description of an atomic absorption spectrophotometer with respect to FIG. 4, only those features of such a spectrophotometer have been mentioned which are relevant to the invention and there are other features which conventionally are present or may be present. For example, the lamp power supply is normally modulated and the signal from the detector DET is correspondingly demodulated prior to processing by the logarithmic converter LG. Also the detector DET will be subject to gain control which may be automatic. Also double beam operation, that is the provision of a reference optical path which bypasses the atomiser and the use of the signal derived via this reference path to provide baseline correction which counteracts instrumental drift, particularly of the hollow cathode lamp output and the detector output, is a well known optional feature of atomic absorption spectrophotometers. In the case of the spectrophotometer described above with reference to FIG. 4 which is capable of automatic operation for a long period of time, double beam operation will be particularly advantageous and very likely incorporated.

Referring now to FIG. 5, there is shown a flow chart of an operation of the spectrophotometer shown in FIG. 4.

In operation 1 "Switch On" the user switches on the electrical supplies to the spectrophotometer. In operation 2 "Initialise", the user ensures that the four single atomic element hollow cathode lamp assemblies HCL1 to HCL4 are loaded by being located in the turret TU and electrically connected, and that four corresponding information sets are located in the non-volatile read-write memory NVM. There will be only one loading position for the lamps which will coincide with the position in which a lamp is located on the optical axis of the spectrophotometer, that is to say the position of the lamp assembly HCL1 as shown in FIG. 4. As each lamp assembly is loaded in turn the microprocessor μP can transfer the relevant atomic element related information for the respective information set from the read-only memory ROM into an appropriate location in the non-volatile memory NVM responsive to measurement of the respective one of the lamp assembly networks RN1 to RN4 by the measurement circuit means MCM. At the time that each lamp is in the loading position the user can enter the relevant sample related information for the respective information set into the memory NVM via the key pad KPD and the microprocessor μP. It may be that the operation of the spectrophotometer is to be a repeat, for a new set of samples in the automatic sampler AS, of an immediately preceding analysis sequence for a different set of samples in respect of the atomic elements of the same lamp assemblies HCL1 to HCL4. If this is the case, the lamp assemblies will already be loaded and the corresponding information sets will be present in the non-volatile memory NVM prior to "Switch On" and the "Initialise" operation 2 will not need to be performed by the user. In operation 3 "Power to Lamps" the user switches on the lamp power supply means LPS to each lamp in turn and responsive to this action for each lamp in turn the appropriate lamp current information is derived from the non-volatile memory NVM by the microprocessor μP and applied to the lamp current supply means LPS. In the case where the atomiser AT is of the flame type an operation (not shown) after either operation 2 or 3 and involving action by the user is required to ignite the flame of the atomiser AT. In operation 4 "Start Automatic Sampler" the user initialises the operation of the automatic sampler AS, and responsive to this operation appropriate information is entered from the automatic sampler control means ASC into the read-write memory RAM after which the operation of the spectrophotometer can be entirely automatic under control of the microprocessor μP without further intervention by the user.

Responsive to operation 4, the microprocessor μP performs operation 5 "Set N=1". N represents a turret couznt. The turret count N determines which one of the four lamp assemblies HCL1 to HCL4 should be in the optical path for the duration of a run of the automatic sampler AS, that is to say an analysis of the samples therein for one atomic element, and it also determines which information set in the non-volatile memory NVM will be used by the microprocessor µP during that analysis. The turret count N is held in the read-write memory RAM for the duration of each analysis. Responsive to operation 5, the microprocessor µP performs operation 6 "Set Lamp Turret to N". In this operation the turret TU is driven to position N (At this stage N=1 corresponding to say the lamp assembly HCL1) by the turret control means TUC. Responsive to operation 6, the microprocessor µP controls operation 7 "Set Slits" in which the monochromator MN slit width is set by the slit control means MSC using slit width information from the information set in the non-volatile memory NVM, and then the microprocessor µP controls operation 8 "Set Wavelength" in which the monochromator MN wavelength is set by the wavelength control means MWC using wavelength information from the information set in the non-volatile memory NVM. As is conventional, the gain of the detector DET will be automatically adjusted in conjunction with setting the monochromator wavelength. Also responsive to operation 6 the microprocessor µP will transfer measurement time information from the non-volatile memory NVM to the volatile read-write memory RAM for use by the microprocessor µP during subsequent maasurements of the samples for the one atomic element.

Following operation 8, the microprocessor µP controls operation 9 "Measure Blank". In this operation, under control of the automatic sampler control means ASC, the automatic sampler AS provides a sample to the atomiser AT having nominally zero concentration of the one atomic element for which the set of samples are to be analysed. This sample is atomised by the atomiser AT under control of the atomiser control means ATC, and the output signal of the detector DET is passed via the logarithmic converter LG and the multiplexer MPX2 and analogue-to-digital converter ADC of the measurement circuit means MCM to the microprocessor µP and the result is stored in the read-write memory RAM as a baseline measurement representing zero concentration of the atomic element for the duration of the analysis of the set of samples for that atomic element. In the case where the atomiser AT is of the flame type, the microprocessor µP will apply fuel type and fuel rate information from the non-volatile memory NVM to the atomiser control means ATC for the atomisation of this and all subsequent samples in the analysis for the particular atomic element. In the case where the atomiser AT is of the electrothermal furnace type, the microprocessor µP will apply furnace heating cycle information from the non-volatile memory NVM to the atomiser control means ATC for the atomisation of this and all subsequent samples in the analysis for the particular atomic element. Following operation 9, the microprocessor µP controls operation 10 "Measure Standards". In this operation, a predetermined number of standard, i.e. known concentration samples, which number is present in the relevant information set in the non-volatile memory NVM, are provided in turn by the automatic sampler AS to the atomiser AT. In each case the detector DET output signal is fed via the measurement circuit means MCM to the microprocessor µP and an absorbance result is calculated by comparison with the baseline measurement in the read-write memory RAM and then stored in the read-write memory RAM.

Following operation 10, the microprocessor µP performs operation 11 "Calibration". In this operation the microprocessor µP derives the known concentration values of the standard samples from the relevant information set in the non-volatile memory NVM and uses these concentration values together with the absorbance results for the standard samples, which have been stored in the read-write memory RAM in operation 10, to calculate a set of calibration coefficients which are then stored in the read-write memory RAM for the duration of the analysis for the one atomic element. These calibration coefficients enable the functions conventionally known as scale expansion and curvature correction to be applied to subsequent sample measurements.

Following operation 11, the microprocessor µP controls operation 12 "Measure Sample, Calculate and Store Concentration". In this operation, a sample from the set of samples which is to be analysed in respect of the single atomic element is provided by the automatic sampler AS to the atomiser AT. The absorbance result for that sample derived from the output signal of the detector DET is applied to the read-write memory RAM, the calibration coefficients in the read-write memory RAM are applied to the absorbance result to produce a concentration result, and the concentration result is stored in the read-write memory RAM. Following operation 12, the microprocessor µP controls operation 13 "Automatic Sampler End?". In this operation the automatic sampler control means ASC senses whether or not the automatic sampler AS has reached the end of its run and does not have a further sample to be measured. If the answer is "No", operation 12 is repeated for the next sample. When operation 12 has been performed for all the samples and their respective concentration results stored in the read-write memory RAM, the next operation 13 will produce the answer "yes" and the microprocessor µP will proceed to operation 14 "N=Limit?". In this operation the turret count N is checked to determine whether or not it corresponds to the number of turret positions, for example four turret positions as shown in FIG. 4. For the first analysis N=1 as set by operation 5, and so operation 14 produces the answer "No" in response to which the microprocessor µP performs operation 15 "N=N+1" in which it increments the value of the turret count N. Responsive to operation 15, the microprocessor µP performs operation 6 in which the turret TU is driven to the next position to bring the next lamp assembly HCL2 into the optical path of the spectrophotometer and operations 7 to 13 are repeated to provide another set of concentration results in the read-write memory RAM for the same set of samples in the autosampler AS in respect of the single atomic element of the next lamp assembly HCL2. When eventually operation 14 produces the answer "Yes" the microprocessor µP performs operation 16 "Print Formated Results and Stop". In this operation the concentration results of all the samples of the set of samples in the automatic sampler AS in respect of the atomic elements of all the single atomic element lamp assemblies HCL1 to HCL4 in the turret TU are extracted from the read-write memory RAM in formated form and printed by the printer PRI and the spectrophotometer is then stopped, that is to say most of the electrical supplies are switched off and a dormant condition is set. An analysis sequence for a new set of samples will then require the user to start the whole sequence of operations from operation 1.

We claim:

1. An atomic absorption spectrophotometer source lamp assembly comprising
lamp means for producing resonance line radiation characteristic of at least one atomic element,
electrical network means for representing radiation, and
connecting circuit means for connecting said network means to a circuit enabling identification of said at least one atomic element.

2. A lamp assembly according to claim 1, wherein said network means includes a plurality of electrical resistors.

3. A lamp assembly according to claim 1, wherein said lamp means produces resonance lines for a multiple atomic element hollow cathode lamp.

4. A lamp assembly according to claim 1, wherein said lamp means produces resonance lines for a single atomic element hollow cathode lamp.

5. A lamp assembly according to claim 4, wherein said single atomic element is represented by ohmic values of two resistors of said network.

6. A lamp assembly according to claim 5, wherein one of said two resistors represents tens values and another of said two resistors represents units values of the atomic number of said atomic element.

7. A lamp assembly according to claim 6, wherein said network means represents lamp operating currents for said lamp means.

8. A lamp assembly according to claim 7, wherein said lamp operating current is represented by ohmic values of two other resistors of said network means.

9. A lamp assembly according to claim 8, wherein said lamp means includes a sealed envelope, electrodes within said envelope, and a base structure attached to said envelope, and wherein said electrical network means is located within said base structure.

10. A lamp assembly according to claim 6, wherein said lamp means includes a sealed envelope, electrodes within said envelope, and a base structure attached to said envelope, and wherein said electrical network means is located within said base structure.

11. A lamp assembly according to claim 5, wherein said network means represents lamp operating currents for said lamp means.

12. A lamp assembly according to claim 5, wherein sa lamp means includes a sealed envelope, electrodes within said envelope, and a base structure attached to said envelope, and wherein said electrical network means is located within said base structure.

13. A lamp assembly according to claim 4, wherein said network means represents lamp operating currents for said lamp means.

14. A lamp assembly according to claim 4, wherein said lamp means includes a sealed envelope, electrodes within said envelope, and a base structure attached to said envelope, and wherein said electrical network means is located within said base structure.

15. An atomic absorption spectrophotometer comprising
source lamp assembly means for producing radiation characteristic of at least one atomic element, said source lamp assembly means including lamp means for producing resonance line radiation characteristic of said atomic element, electrical network means for representing said radiation, and connecting circuit means for connecting said network means to a circuit enabling identification of said atomic element,
measurement circuit means for identifying said atomic element, said measurement circuit means being connected to said network means through said connecting means,
atomizer means for atomizing samples to be analyzed by said radiation,
monochromator circuit means for providing measurement wavelengths of said samples, said monochromator circuit means including a monochromator receiving radiation passed by said atomizer means,
detector means for detecting said measurement wavelengths, said detector means being connected to said measurement circuit means
microcomputer circuit means connected to elements of the spectrophotometer for controlling said spectrophotometer, said microcomputer means including
microprocessor means for identifying said atomic element and for applying information to said monochromator circuit means, and
read-only memory circuit means for holding wavelength information associated with said atomic element, said wavelength information being applied to said monochromator circuit means by said microprocessor means.

16. A spectrophotometer according to claim 15, wherein said network means represents lamp operating current for said lamp means.

17. A spectrophotometer according to claim 16, wherein lamp power supply means for operating said lamp means are provided, and wherein said read-only memory circuit means holds lamp current information, said microprocessor means controlling said lamp power supply means by lamp current information from both said measurement circuit means and network means and by said lamp current information from said read-only memory circuit means.

18. A spectrophotometer according to claim 15, wherein read-write memory circuit means is provided for continuously storing at least one information set, said microprocessor means controlling said lamp assembly means with said information set for analyzing said samples with respect to said at least one atomic element, said microprocessor means using said information set for at least a duration of analysis, and wherein said information set has atomic element information derived from said read-only memory circuit means, and from other sample related information.

19. A spectrophotometer according to claim 18, wherein holding and positioning means are provided for holding a plurality of lamp assembly means having said network means for all of said lamp assembly means being connected to said measurement circuit means, said holding and positioning means being provided for positioning one lamp means at a time of said plurality of lamp assembly means in an optical path of both said atomizer means and said monochromator circuit means, and wherein said microprocessor means controls said holding and positioning means, to position said radiation characteristics of each atomic element in said optical path, said microprocessor means using each of a plurality of said information sets in turn, said plurality of information sets being continuously stored in said read-write memory circuit means at least for said duration of analysis.

20. A spectrophotometer according to claim 19, wherein said network means includes a plurality of electrical resistors.

21. A spectrophotometer according to claim 20, wherein said atomic element is represented by ohmic values of two resistors of said network means.

22. A spectrophotometer according to claim 21, wherein one of said two resistors represents tens values and another of said two resistors represents units values of the atomic number of said atomic element.

23. A spectrophotometer according to claim 22, wherein said network means represents lamp operating current for said lamp means, and wherein said lamp operating current is represented by ohmic values of two other resistors of said network means.

24. A spectrophotometer according to claim 15, wherein said network means includes a plurality of electrical resistors.

25. A spectrophotometer according to claim 24, wherein said atomic element is represented by ohmic values of two resistors of said network means.

26. A spectrophotometer according to claim 25, wherein one of said two resistors represents tens values and another of said two resistors represents units values of the atomic number of said atomic element.

27. A spectrophotometer according to claim 26, wherein said network means represents lamp operating current for said lamp means, and wherein said lamp operating current is represented by ohmic values of two other resistors of said network means.

28. An atomic absorption spectrophotometer according to claim 15, wherein said circuit enabling identification of said atomic element includes at least one multiplexer circuit means connected to said electrical network means for providing multiplexed signals and an analog-digital converter means connected to said multiplexer circuit means for receiving each said multiplexed signal respectively, said analog-digital converter means providing output signals representative of said electrical network means.

29. An atomic absorption spectrophotometer comprising
source lamp assembly means for producing radiation characteristic of at least one atomic element, said source lamp assembly means including at least one lamp means for producing resonance line radiation characteristic of said atomic element, electrical network means for representing said radiation, and connecting circuit means for connecting said network means to measurement circuit means for enabling identification of said atomic element, and
microprocessor means coupled to said measurement circuit means for providing said identification of said atomic element in response to measurement of said network means by said measurement circuit means.

30. An atomic absorption spectrophotometer according to claim 29, wherein said measurement means includes at least one multiplexer circuit means connected to said electrical network means for providing multiplexed signals and an analog-digital converter means connected to said multiplexed circuit means for receiving each of said multiplexed signals, respectively, said analog-digital converter means providing output signals representative of said electrical network means.

31. An atomic absorption spectrophotometer according to claim 30, wherein said electrical network means includes a plurality of electrical resistors.

32. An atomic absorption spectrophotometer according to claim 29, wherein holding and positioning means are provided for holding more than one said lamp means at a time, said network means of said more than one lamp means being connected to said measurement circuit means, and wherein said microprocessor means identifies atomic elements of each of said more than one lamp means.

33. An atomic absorption spectrophotometer according to claim 29, wherein said network means represents lamp operating current for said lamp means.

34. An atomic absorption spectrophotometer according to claim 33, wherein said microprocessor means identifies said lamp operating current.

* * * * *

UNITED STATES PATENT AND TRADEMARK OFFICE
CERTIFICATE OF CORRECTION

PATENT NO. : 4,669,879

DATED : June 2, 1987

INVENTOR(S) : Trevor Stockdale ET AL

It is certified that error appears in the above-identified patent and that said Letters Patent is hereby corrected as shown below:

Col. 3, line 47, change "cx;nsidered" to --considered--

Col. 9, line 43, change "mesory" to --memory--

Col. 10, line 67, change "couznt" to --count--

Signed and Sealed this

Twenty-ninth Day of March, 1988

Attest:

DONALD J. QUIGG

*Attesting Officer*  *Commissioner of Patents and Trademarks*